United States Patent

Fujiwara et al.

[11] Patent Number: 5,146,097
[45] Date of Patent: Sep. 8, 1992

[54] METHOD FOR MEASURING GLOSS PROFILE

[75] Inventors: Hideki Fujiwara; Chizuru Kaga; Isao Kano, all of Tokyo, Japan

[73] Assignee: Jujo Paper Co., Ltd., Tokyo, Japan

[21] Appl. No.: 699,641

[22] Filed: May 14, 1991

[30] Foreign Application Priority Data

May 15, 1990 [JP] Japan .................. 2-124440

[51] Int. Cl.$^5$ ........................... G01N 21/57
[52] U.S. Cl. ................. 250/372; 250/359.1; 356/446
[58] Field of Search ............... 250/372, 359.1, 358.1; 356/445, 446

[56] References Cited

U.S. PATENT DOCUMENTS

| | | | |
|---|---|---|---|
| 3,395,278 | 7/1968 | McDivitt | 250/372 |
| 4,124,808 | 11/1978 | Bowers | 250/359.1 |
| 4,697,082 | 9/1987 | Bartewen | 250/359.1 |
| 4,831,264 | 5/1989 | Fujiwara | 250/372 |
| 4,937,449 | 6/1990 | Kreuzer et al. | 250/359.1 |
| 5,066,865 | 11/1991 | Wennerberg | 356/446 |
| 5,078,496 | 1/1992 | Parker et al. | 356/446 |

Primary Examiner—Carolyn E. Fields
Assistant Examiner—Drew A. Dunn
Attorney, Agent, or Firm—Sherman and Shalloway

[57] ABSTRACT

This invention relates to a method for measuring a gloss profile of the surface of materials as paper, specifically coated paper, synthetic resin film, metals and the like.

This method comprises the step of applying a spot of a monochromatic ultraviolet light to the surface of sample, moving the spot on the surface of the sample, photoelectrically converting a reflected light of each spot, obtained with a same reflective angle as an incident angle, and comparing and calculating the reflectance to determine the gloss profile.

3 Claims, 2 Drawing Sheets

METHOD FOR MEASURING GLOSS PROFILE

BACKGROUND OF THE INVENTION

This invention relates to a method for measuring a gloss profile of the surface of such materials as paper, synthetic resin films, metals, and the like.

Various materials have a gloss, and, in most cases, it is desirable that the gloss is uniform. The gloss profile, depending on its degree, may affect the product values.

In paper, for example, the apparent evenness of its surface is called a "sheet appearance," which is a very important factor for the evaluation of paper quality. The sheet appearance is substantially evaluated in terms of the uniformity of whiteness and gloss of the paper surface and the paper thickness. If there are any unevenness in these factors, the paper is evaluated to have a low sheet appearance. The cause for surface unevenness of paper includes fluctuations in the basis weight and caliper during the paper manufacturing process, which leads to a low sheet appearance. As for coated paper, which is coated on the surface with pigments, the purpose of coating is to improve the surface smoothness, brightness and opacity. Therefore, an uneven gloss profile means an imperfect coating purpose, resulting in a defective product. In particular, "orange peel," a fine unevenness that occurs in the coated surface, is greatly related with the gloss profile.

Under such circumstances, the presence and degree of gloss profile in coated paper has a great significance in the process control of the coated paper production. However, in an actual process control, the gloss profile is not directly evaluated, but the emphasis of the evaluation is placed more on the sheet appearance. However, the evaluation depends greatly on the inspector's subjective, less consistent evaluation criteria. Therefore, a more objective and exact evaluation method has been in demand.

Heretofore, there has been used a surface roughness tester as a method for measuring the surface roughness by a physical contact. This method is effective for measuring a roughness of the micron level, however, since fine surface irregularities have a smaller pitch than that detectable as gloss profile by the human eye. Therefore, it is not directly connected with gloss profile.

Further, Japanese Patent Publication 1-24256 discloses a three-dimensional optical device comprising a light source and a light receiver, capable of varying the incident angle and the reflection angle of the sample. This device is used to measure the tone of color from the brilliance and brightness of a metallic coating.

Since gloss profile is a fluctuation condition of glossiness, it can be determined as a distribution of glossiness. Therefore, it is possible to measure the gloss profile using the above-described three-dimensional optical device. However, since this optical device uses a tungsten lamp as a light source, filtered to obtain a white light, it is suitable to measure the tone of color, but is not always suited for measuring the gloss profile.

With a view toward obviating above prior art defects, it is a primary object of the present invention to provide a method for measuring a gloss profile of the sample surface, more specifically, a simple method for measuring a sheet appearance of coated paper rapidly and accurately.

SUMMARY OF THE INVENTION

The inventors have investigated a light source and a wavelength which are most suitable for measuring the gloss profile. As a result, it has been found that monochromatic ultraviolet light, particularly, an ultraviolet light in the vicinity of 220 nm in wavelength, having a spot size of 0.1 to 3.0 mm, more preferably 0.1 to 1.0 mm, is most suitable.

Thus, in accordance with the present invention, in a first preferred embodiment, based on the above findings, there is provided a method for measuring a gloss profile comprising the steps of applying a spot of monochromatic ultraviolet light to the surface of a sample to be measured, regularly moving the spot on the surface of a predetermined area of the sample, photoelectrically converting a reflected light of each spot, and comparing the reflectance of individual spots to determine a uniformity of gloss.

In a second preferred embodiment, in addition to the first embodiment, the present invention is further characterized in that the spot of monochromatic ultraviolet light is a polygonal spot of 0.1 to 3.0 mm on a longest side, or a circular or elliptical spot having a largest diameter of 0.1 to 3.0 mm.

In a third preferred embodiment, in addition to the first or second embodiment, the present invention is further characterized in that the wavelength of the monochromatic light is 210 to 230 nm.

In the present invention, it is necessary that the incident angle and the reflective angle are equal to each other with respect to the sample surface. An angle of 75 degrees is most widely used for measuring the glossiness of paper, which is most suitable for the purpose. However, the angle is not limited to this, but basically any other angles can be used, for example, 60 degrees, 45 degrees, 30 degrees, and so on.

Since gloss is a problem in visible light, prior art gloss meters naturally use visible light wavelengths of 400 to 800 nm, and its white light is used. On the other hand, the present invention uses a monochromatic ultraviolet light.

FIG. 1 is a diagram plotting correlation coefficients showing the relationship between a signal value, proportional to a current obtained by photoelectrically converting the reflected light of 10 samples of coated paper, illuminated with monochromatic light of different wavelengths ranging from visible light to ultraviolet light, measured by the method according to the present invention, and a glossiness measured by a gloss meter according to JIS P-8142.

From FIG. 1, it is clear that ultraviolet light is higher in correlation than visible light, and that ultraviolet light of 210 to 230 nm in wavelength is most preferable. Therefore, ultraviolet light is preferable over visible light in order to measure the gloss profile accurately and quickly, which indicates the behavior of glossiness on the surface of the sample.

Furthermore, accurate measurement can be achieved by using a polygonal spot of monochromatic ultraviolet light of 0.1 to 3.0 mm on a longest side, or a circular or elliptical spot having a largest diameter of 0.1 to 3.0 mm. This agrees well with the fact that visual determination mainly relates to fine irregularities of less than 3 mm in size.

Figure 1:
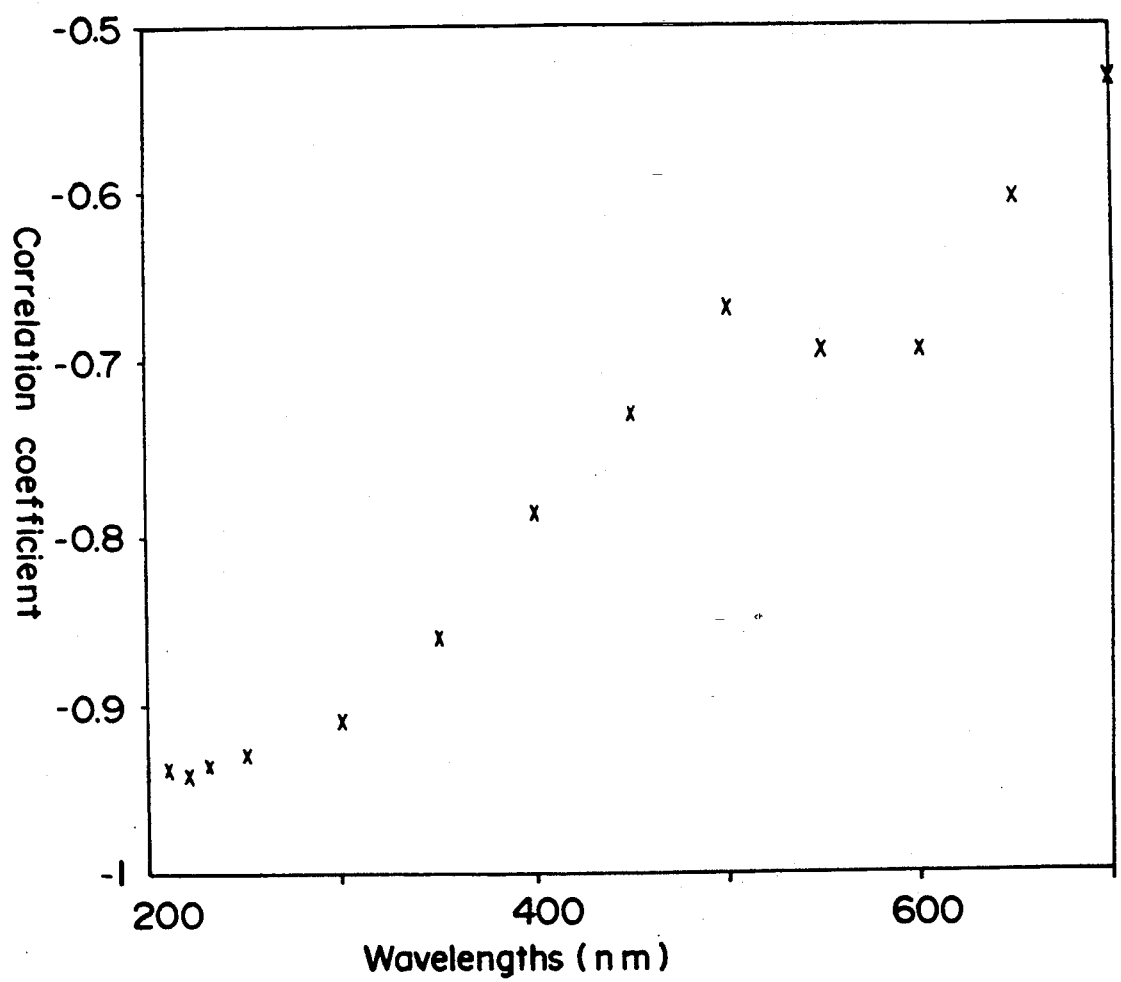
FIG. 1 is a diagram plotting correlation coefficients showing the relationship between a signal value, proportional to a current obtained by photoelectrically converting the reflected light of 10 samples of coated paper, applied with monochromatic light of different wavelengths ranging from visible light to ultraviolet light, measured by the method according to the present invention, and a glossiness measured by a gloss meter according to JIS P-8142.

In the figures, numeral 1 indicates a detector, numeral 4 indicates a deuterium lamp, numeral 5 indicates a filter, numeral 7 indicates a half mirror, numeral 10 indicates a sample base, and numeral 21 indicates a stepping motor.

DESCRIPTION OF PREFERRED EMBODIMENTS

Figure 2:
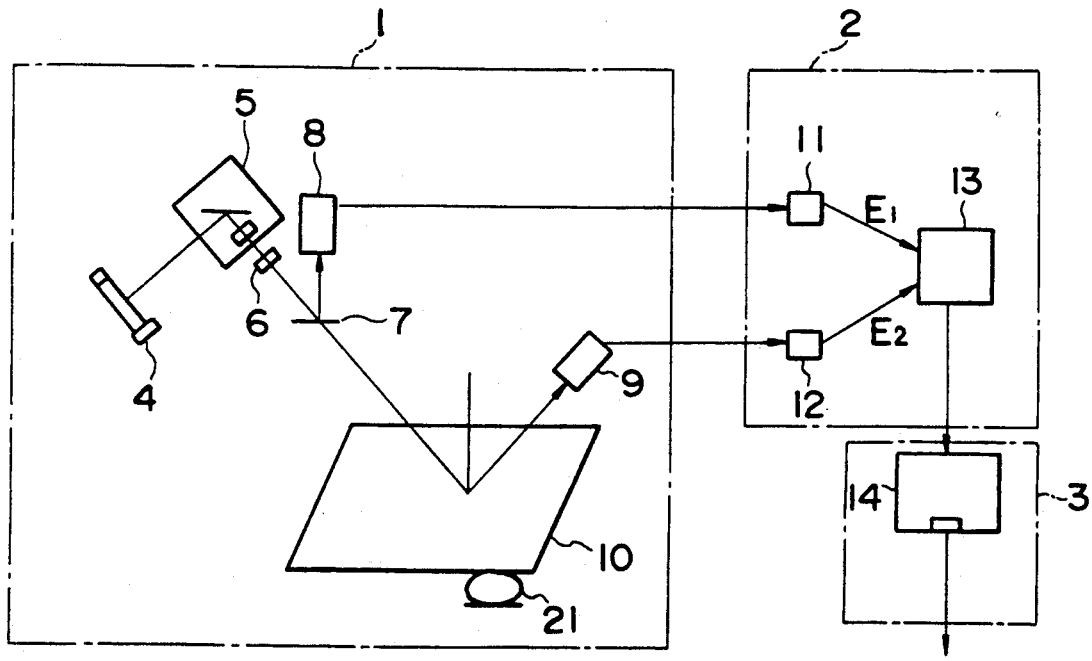
FIG. 2 is a schematic view showing the arrangement of a device used for the method according to the present invention.

Preferred embodiments of the present invention will now be described. FIG. 2 is a schematic view showing the arrangement of a device used in the measurement according to the present invention. This device mainly comprises a detector 1, a converter amplifier 2, and an external output unit 3.

The detector 1 comprises a deuterium lamp 4, a filter 5, a diaphragm 6, a half mirror 7, a reference light electrophotomultiplier 8, a reflected light electrophotomultiplier 9, and a sample base 10.

To measure a glossiness, ultraviolet light emitted from the deuterium lamp 4 is filtered by the filter by the filter 5 into a monochromatic light with a specific wavelength. The monochromatic light is diaphragmed by the diaphragm 6 into a spot light, and is then separated by the half mirror 7. Part of the separated light is detected as a reference light by the reference light electrophotomultiplier 8. The rest of the separated light is applied to a sample placed on the sample base 10, which is reflected. Part of the reflected light is detected by the reflected light electrophotomultiplier 9. In this case, the incident angle and the reflective angle of the light with respect to the sample must be equal to each other and must be on a same plane. The sample base 10 is an XY stage provided with a stepping motor 21, which can be moved vertically and horizontally at predetermined intervals.

The reference light and the reflected light detected are converted into currents by the electrophotomultipliers 8 and 9, which are then converted into voltages by operational amplifiers 11 and 12 in the converter amplifier 2. The voltages obtained, E1 and E2, are subtracted in a subtraction circuit 13, and then converted into digital signals by an analog/digital converter circuit 14 of the external output unit 3. The digitized signals are transferred to a data processing unit comprising a computer, a recorder, and the like, where the signals are converted.

In the present invention, the digital signals obtained in the analog/digital converter circuit 14 can be converted into a normal glossiness, with reference to a calibration curve of glossiness, previously obtained by measuring a standard sample.

Next, the method according to the present invention used for measuring the gloss profile using the above-described measuring device will now be described.

EXAMPLE 1

From a Japanese A2 grade supercalendered coated paper, 8 types of commercial paper having a basis weight of 84.9 g/m$^2$ were selected as samples. A monochromatic ultraviolet light of 220 nm in wavelength, as a 0.4 mm$\times$0.4 mm spot, the incident angle and the reflective angle adjusted to 75 degrees, was applied to 156 spots over a length of 102 mm within a sample to measure the gloss profile.

The average glossiness and changes in gloss, that is, the standard deviation of the gloss distribution for the individual sample are shown in Table 1, together with the glossiness measured in accordance with JIS P-8142.

On the other hand, visual inspection of the sheet appearance was performed by a staff of 12 inspectors. Their ranking on the sheet appearance based on the total points given by the 12 inspectors is also shown in Table 1.

As can be seen from Table 1, it is understood that the better the sheet appearance, the smaller is the standard deviation of the glossiness. Thus, with the method according to the present invention, not only the gloss profile can be measured, but it is possible to measure the sheet appearance more objectively.

EXAMPLES 2-4

In Examples 2, 3, and 4, a Japanese A2 grade supercalendered coated paper having a basis weight of 127.9 g/m$^2$, and matte grades having basis weights of 81.4 g/m$^2$ and 127.9 g/m$^2$, respectively, were used. For the three types of paper, 8, 6, and 7 commercial papers were selected as samples.

These samples were measured for the average glossiness and the standard deviation using the same procedure as in Example 2. The results are shown in Table 1, together with the ranking of the sheet appearance based on the total points given by the 12 inspectors and the JIS glossiness.

TABLE 1

| | | Sample No. | Sheet appearance ranking | JIS glossiness | Present invention | |
|---|---|---|---|---|---|---|
| | | | | | Average glossiness | Standard deviation |
| Ex. 1 | Super-calendered grade 84.9 g/m$^2$ | 1 | 2 | 62.9 | 62.9 | 1.16 |
| | | 2 | 4 | 64.2 | 66.4 | 1.13 |
| | | 3 | 5 | 68.6 | 69.3 | 1.20 |
| | | 4 | 7 | 64.9 | 64.5 | 1.45 |
| | | 5 | 1 | 71.2 | 68.6 | 0.93 |
| | | 6 | 8 | 65.0 | 67.0 | 1.53 |
| | | 7 | 5 | 57.2 | 58.5 | 1.43 |
| | | 8 | 3 | 62.3 | 63.8 | 1.33 |
| Ex. 2 | Super-calendered grade 127.9 g/m$^2$ | 9 | 4 | 96.4 | 69.0 | 1.18 |
| | | 10 | 8 | 64.6 | 65.9 | 1.38 |
| | | 11 | 2 | 68.9 | 69.0 | 0.81 |
| | | 12 | 4 | 67.9 | 66.3 | 0.97 |
| | | 13 | 1 | 71.8 | 72.2 | 1.05 |

TABLE 1-continued

|  | Sample No. | Sheet appearance ranking | JIS glossiness | Present invention | |
|---|---|---|---|---|---|
|  |  |  |  | Average glossiness | Standard deviation |
|  | 14 | 3 | 64.2 | 65.7 | 1.09 |
|  | 15 | 7 | 69.0 | 71.8 | 1.37 |
|  | 16 | 4 | 64.6 | 65.2 | 1.10 |
| Ex. 3 Matte grade 81.4 g/m$^2$ | 17 | 4 | 10.3 | 17.6 | 0.95 |
|  | 18 | 1 | 22.2 | 19.6 | 0.32 |
|  | 19 | 6 | 15.1 | 15.4 | 1.41 |
|  | 20 | 2 | 20.6 | 22.5 | 0.53 |
|  | 21 | 3 | 19.9 | 20.8 | 0.47 |
|  | 22 | 4 | 23.6 | 24.9 | 0.61 |
| Ex. 4 Matte grade 127.9 g/m$^2$ | 23 | 5 | 12.4 | 12.0 | 0.92 |
|  | 24 | 6 | 28.7 | 27.2 | 1.10 |
|  | 25 | 1 | 23.3 | 20.7 | 0.48 |
|  | 26 | 6 | 17.4 | 18.3 | 1.63 |
|  | 27 | 2 | 15.9 | 14.7 | 0.74 |
|  | 28 | 3 | 22.7 | 23.4 | 0.55 |
|  | 29 | 4 | 19.1 | 20.8 | 0.77 |

REFERENCE EXAMPLE 1

From the above-described Examples 1 to 4, it is clear that the standard deviation of the glossiness and the sheet appearance agree with each other. The same samples were tested for other properties which are considered to be related to the sheet appearance: glossiness, opacity, brightness, Bekk smoothness, and Parker print surf smoothness (PPS smoothness). Furthermore, the correlation coefficients were determined between the test results and the ranking on sheet appearance for the individual samples. The results are shown in Table 2. The correlation coefficients are also shown between the standard deviation of glossiness according to the present invention and the ranking of sheet appearance evaluation.

TABLE 2

|  | Example | | | |
|---|---|---|---|---|
|  | 1 Super-calendered grade | 2 Super-calendered grade | 3 Matte grade | 4 Matte grade |
| Basis wt. (g/m$^2$) | 84.9 | 127.9 | 81.4 | 127.9 |
| No. of sample | 8 | 8 | 6 | 7 |
| St. deviation of glossiness | 0.85 | 0.83 | 0.91 | 0.83 |
| Glossiness | 0.21 | 0.43 | 0.53 | 0.00 |
| Opacity | 0.24 | −0.57 | −0.64 | 0.00 |
| Brightness | 0.33 | −0.53 | −0.26 | −0.38 |
| Bekk smoothness | −0.04 | −0.21 | −0.03 | 0.28 |
| PPS smoothness | 0.67 | 0.36 | −0.01 | −0.12 |

As a result, the only case where a correlation of 0.8 or higher is always observed is in the standard deviation of glossiness determined by the present invention. However, the sheet appearance cannot be evaluated from the absolute value of glossiness, opacity or brightness, nor from Bekk or PPS smoothness.

EXAMPLE 5

A black-painted steel plate was used as a sample, which was irradiated with a monochromatic ultraviolet spot light with a wavelength of 280 mm, measuring 0.2 mm×0.2 mm, with incident and reflective angles set to 60 degrees with respect to the sample. Measurement was made over an area of 15 mm×15 mm at 1 mm intervals (vertically and horizontally). The measured spots were 16×16 (vertically and horizontally, with a total of 256 spots.

The test results showed an average glossiness of 88.57, and a standard deviation of glossiness of 0.78. It was confirmed from these values that this sample has a relatively small gross profile, with a fairly good surface condition.

With the method for measuring the gloss profile according to the present invention, the gloss profile can be optically measured using a monochromatic ultraviolet light. Furthermore, the standard deviation of the glossiness, which indicates a distribution of gloss, well corresponds with the sheet appearance of coated paper, for which it has been a problem in that the evaluation of sheet appearance has relied heavily upon the visual inspection by individual inspectors. Thus, with the present invention, it is possible to measure the gloss profile and the sheet appearance objectively, quickly and accurately.

The present is not limited to the above coated paper, but can also be applied to such materials as paper, synthetic resins, metals, glass and the like, which can be measured for the gloss profile.

What is claimed is:

1. A method for measuring a gloss profile comprising the steps of applying a spot of a monochromatic ultraviolet light to the surface of a sample to be measured; regularly moving said spot on the surface of a predetermined area of the sample; photoelectrically converting a reflected light of each spot, obtained with a same reflective angle as an incident angle, and comparing and calculating the reflectance to determine the gloss profile.

2. The method of claim 1, wherein said spot of monochromatic ultraviolet light is a polygonal spot of 0.1 to 3.0 mm on a longest side, or a circular or elliptical spot having a largest diameter of 0.1 to 3.0 mm.

3. The method of claim 1 or claim 2, wherein said monochromatic ultraviolet light has a wavelength of 210 to 230 nm.

* * * * *